(12) United States Patent
Burge et al.

(10) Patent No.: US 12,281,296 B2
(45) Date of Patent: Apr. 22, 2025

(54) ELECTROCHEMICAL MICROBIAL SENSOR SYSTEM AND METHOD OF USING SAME

(71) Applicant: Burge Environmental, Inc., Tempe, AZ (US)

(72) Inventors: Scott R. Burge, Tempe, AZ (US); David A. Hoffman, Tempe, AZ (US)

(73) Assignee: Burge Environmental, Inc., Tempe, AZ (US)

( * ) Notice: Subject to any disclaimer, the term of this patent is extended or adjusted under 35 U.S.C. 154(b) by 203 days.

(21) Appl. No.: 17/244,440

(22) Filed: Apr. 29, 2021

(65) Prior Publication Data

US 2021/0246412 A1 Aug. 12, 2021

Related U.S. Application Data

(63) Continuation of application No. 16/054,789, filed on Aug. 3, 2018, now abandoned.

(60) Provisional application No. 62/586,602, filed on Nov. 15, 2017, provisional application No. 62/570,186, filed on Oct. 10, 2017, provisional application No. 62/541,338, filed on Aug. 4, 2017.

(51) Int. Cl.
| | |
|---|---|
| *G01N 27/00* | (2006.01) |
| *C12M 1/34* | (2006.01) |
| *C12M 3/00* | (2006.01) |
| *G01N 27/404* | (2006.01) |
| *G01N 27/411* | (2006.01) |
| *G01N 33/18* | (2006.01) |
| *G01N 33/24* | (2006.01) |
| *G01N 27/403* | (2006.01) |

(52) U.S. Cl.
CPC .......... *C12M 41/46* (2013.01); *G01N 27/404* (2013.01); *G01N 27/411* (2013.01); *G01N 33/1806* (2013.01); *G01N 33/24* (2013.01); *C12M 41/32* (2013.01); *G01N 27/4035* (2013.01)

(58) Field of Classification Search
CPC ..... C12M 41/46; C12M 41/32; G01N 27/404; G01N 27/411; G01N 27/4035; G01N 33/1806; G01N 33/24
USPC .......................................... 434/34
See application file for complete search history.

(56) References Cited

U.S. PATENT DOCUMENTS

| | | | | |
|---|---|---|---|---|
| 5,254,461 | A | * | 10/1993 | Rohrback ............... C12Q 1/06 422/77 |
| 6,113,762 | A | * | 9/2000 | Karube ................. C12Q 1/004 204/403.06 |
| 9,299,999 | B2 | * | 3/2016 | Chang .................... H01M 8/16 |
| 2014/0048424 | A1 | * | 2/2014 | Gu ......................... G01N 17/02 204/404 |

(Continued)

*Primary Examiner* — Nathan A Bowers
(74) *Attorney, Agent, or Firm* — SNELL & WILMER L.L.P.

(57) ABSTRACT

A microbial sensor, system and method that can be used to determine the chemical environment and/or substrate concentrations in saturated and unsaturated natural and environments, such as soils, aquifers and sediments are disclosed. The system may be used for monitoring municipal and industrial treatment facilities and sites where chemicals or contaminants were released to natural environments. The electrochemical microbial sensor system can be referenced using either a cathode exposed to oxygen or a reference cell (silver/silver chloride or calomel) for monitoring natural or man-made environments.

10 Claims, 10 Drawing Sheets

(56) References Cited

U.S. PATENT DOCUMENTS

2017/0045470 A1\* 2/2017 Burge ................ G01N 27/4163

\* cited by examiner

ELECTROCHEMICAL MICROBIAL SENSOR SYSTEM AND METHOD OF USING SAME

CROSS-REFERENCE TO RELATED APPLICATIONS

This application is a continuation of U.S. Non-Provisional application Ser. No. 16/054,789, filed Aug. 3, 2018, and entitled "Electrochemical Microbial Sensor System and Method of Using Same," which claims the benefit of U.S. Provisional Application No. 62/541,338, filed Aug. 4, 2017, and entitled "Universal Field Deployment System for Microbial Sensor Systems for Monitoring Industrial, Waste, Natural and Groundwater," U.S. Provisional Application No. 62/570,186, filed Oct. 10, 2017, and entitled "Microbial Sensor System for Monitoring the Rhizosphere and Adjacent Soils," and U.S. Provisional Application No. 62/586,602, filed Nov. 15, 2017, and entitled "Microbial Sensor System for Monitoring Sediments, Natural and Waste Waters." The contents of the above provisional applications are incorporated herein by reference to the extent such contents do not conflict with the present disclosure.

STATEMENT REGARDING FEDERALLY SPONSORED RESEARCH OR DEVELOPMENT

This invention was made with government support by the Office of Science grant DE-FOA-0001405 awarded by the Department of Energy. The government has certain rights in the invention.

FIELD OF DISCLOSURE

The present disclosure generally relates to microbial sensors and systems, and to methods of using the sensors and systems. More particularly, the present disclosure relates to sensors and systems that employ open-circuit voltage and/or recovery voltage measurements to provide information concerning microbial activity, reduction/oxidation conditions and/or substrate concentrations of saturated and unsaturated environments.

BACKGROUND OF THE DISCLOSURE

Microbial fuel cells were developed for the conversion of waste products (sewage, farming wastes, etc.) into electrical energy. However, other applications of microbial fuel cells include use as analytical sensors and in bioremediation. The analytical sensors using microbial fuel cells typically measure the flow of current between the anode and cathode as the metric for determining substrate concentrations and other analytical parameters (e.g., biological oxygen demand, BOD).

Disadvantages of such sensors using a reactor design for analytical applications for characterizing submerged sediments and natural waters include: (1) The reactor design requires the substrate in water to be passed through an anode chamber. This is not a desired option if the anode is being directly inserted in sediments, soils and groundwater. (2) Reconfiguration of reactor designs to match the actual site conditions is difficult and not suitable for a majority of the sites. (3) Most reactor designs are optimized (anode and cathode size, microbial composition, and performance) for energy production that is not an important parameter for an analytical sensor. (4) Reactor design is not convenient for the deployment of multiple sensors to characterize the chemical (oxidizing and reducing) environment of a site. (5) Current measurement to determine microbial activity/substrate concentration may not be sensitive enough to measure desired microbial activity. Accordingly, improved sensors, sensor systems, and techniques for using the sensors and sensor systems are desired.

SUMMARY OF THE DISCLOSURE

Various embodiments of the present disclosure relate to methods and systems for characterizing natural and contaminated saturated environments. While the ways in which various embodiments of the disclosure address the drawbacks of the prior art are discussed in more detail below, in general, the disclosure provides sensors that are relatively sensitive (can detect very low substrate concentrations), have a relatively simple design, have a reconfigurable design—allowing for use of the sensor in a wide variety of applications, and/or can have a relatively long lifetime in the environment, systems including the sensors, and methods of using the sensors and systems. Exemplary sensor systems can be used to, for example, determine: 1) redox conditions using open-circuit voltage measurements, and 2) substrate concentrations performing recovery voltage measurements. Exemplary microbial sensors can connect with control/communication circuitry configured to provide real-time collection of data and/or the transmission of the data using wireless (e.g., cellular) communications to remote users. Exemplary microbial sensors can be used for monitoring natural and contaminated environments, wastewater and industrial treatment facilities, and other environments where redox conditions are an important parameter to be monitored.

In accordance with further exemplary embodiments of the disclosure, field deployment systems for the microbial sensors for a variety of environments are presented. The design of the systems employs commonly available construction materials (e.g., PVC piping) for monitoring a variety of different environments including saturated and unsaturated zones in the environment, industrial wastewater and municipal wastewater treatment facilities.

In accordance with further exemplary embodiments of the disclosure, a reversible cathode capable of monitoring solutions within a piping system and monitoring saturated environments exterior of a piping system is disclosed.

In accordance with further exemplary embodiments of the disclosure, a microbial monitoring system for measurement of redox and other conditions in saturated zones employs a standard reference electrode (e.g., Ag/AgCl, calomel), in lieu of a traditional cathode, as the reference cell. Microbial activity can be measured by measuring a voltage between the reference electrode/cell and one or more anodes populated by biofilms.

In accordance with further exemplary embodiments of the disclosure, a microbial monitoring system includes a standard reference cell, a cathode, and anode (e.g., populated with a biofilm) and control circuitry/measurement device. The control circuitry can be configured to control the flow of current between the cathode and the anode (e.g., covered with a biofilm). The control circuitry/measurement device can be further configured to measure a recovery voltage between the reference cell and anode (e.g., covered with a biofilm).

In accordance with yet further exemplary embodiments of the disclosure, a monitoring system for characterizing a wastewater treatment facility is disclosed. The monitoring system can include separate measurement/communication modules capable of assessing each of the treatment stages within a treatment facility.

BRIEF DESCRIPTION OF THE DRAWING FIGURES

A more complete understanding of exemplary embodiments of the present disclosure may be derived by referring to the detailed description and claims when considered in connection with the following illustrative figures.

It will be appreciated that elements in the figures are illustrated for simplicity and clarity and have not necessarily been drawn to scale. For example, the dimensions of some of the elements in the figures may be exaggerated relative to other elements to help to improve understanding of illustrated embodiments of the present disclosure.

DETAILED DESCRIPTION OF EXEMPLARY EMBODIMENTS OF THE DISCLOSURE

The description of exemplary embodiments of methods, systems, and probes provided below is merely exemplary and is intended for purposes of illustration only; the following description is not intended to limit the scope of the disclosure or the claims. Moreover, recitation of multiple embodiments having stated features is not intended to exclude other embodiments having additional features or other embodiments incorporating different combinations of the stated features.

As noted above, prior microbial sensor technologies (energy production, bioremediation, analytical sensors) are primarily based on the measurement of electrical current between an anode and a cathode. The measurement of constant current allows for the determination of substrate concentration in a solution. In contrast, the inventors surprisingly found that measurements of open-circuit voltage (OCV) and recovery voltage (RV) are capable of providing information distinct from the measurement of constant current and can use less sensitive instrumentation to provide meaningful information regarding substrates and concentrations thereof that are or may be present in an environment.

U.S. patent application Ser. No. 15/237,230, in the name of Burge et al., filed Aug. 15, 2016 (hereinafter "the '230 Application"), discloses a microbial sensor system using open-circuit voltage and recovery voltage as the metric for determining redox conditions and substrate concentrations, respectively. As set forth below, various embodiments of the present disclosure provide alternatives and/or improvements to various designs set forth in the '230 Application. For example, improved anode assemblies, cathode assemblies, sensor systems, and methods of using the same are set forth below.

This disclosure presents a microbial sensor system for monitoring of both saturated and unsaturated zones in natural environments. Additionally, the system can be used to characterize releases of hazardous chemicals to the environments, industrial treatment facilities, and sanitary treatment facilities.

The description below provides examples of various illustrative embodiments of the present disclosure. The examples below are merely illustrative, and unless otherwise noted, the present invention is not limited to such examples.

Embodiment 1

Figure 1:
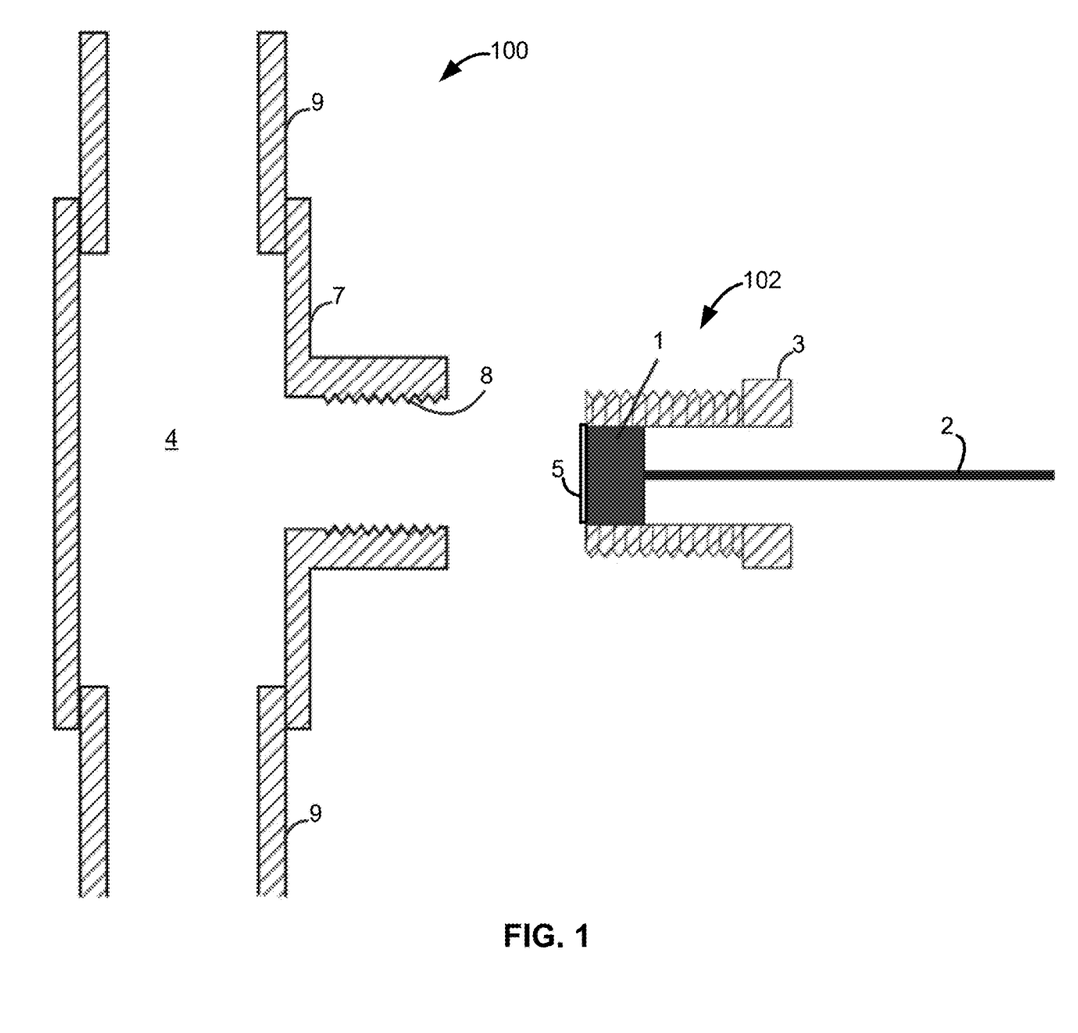
FIG. 1 illustrates an exemplary anode assembly suitable for monitoring solutions within an interior of pipes in accordance with at least one embodiment of the disclosure.

Referring to FIG. 1, a microbial monitoring system 100 for monitoring an area (e.g., a fluid) located within the interior 4 of a pipe 9, is illustrated. System 100 includes an anode assembly 102, including an anode 1, coupled to pipe 9. Pipe 9 can be composed of, for example, polymer pipe, such as commercially-available polychlorinated (PVC) pipe used for water and irrigation applications. In the illustrated example, anode 1 is located within a threaded (e.g., polymer) fitting 3. Anode 1 can be oriented within the threaded polymer fitting 3 to monitor solutions within the interior 4 of the pipe 9. Unthreaded (e.g., polymer) fittings may be used as an alternative to the threaded fitting 3. The anode 1 can be or comprise graphite or other inert material (e.g., gold, titanium, or the like). A microbial biofilm 5 populates the surface of the anode 1. An anode cable 2 electrically connects to the anode 1. The threaded polymer fitting 3 connects to a threaded port 8 of a tee fitting 7. The tee fitting 7 connects to the pipe 9. A slip fitting or other method of attachment may be used in lieu of a threaded fitting 3 and threaded port 8.

Operation

The contents of the interior 4 of the pipe 9 interact with the biofilm 5 located on the surface of the anode 1, creating a voltage. The anode cable 2 is used to transmit the voltage to, for example, a measurement device, described in more detail below.

Embodiment 2

Figure 2:
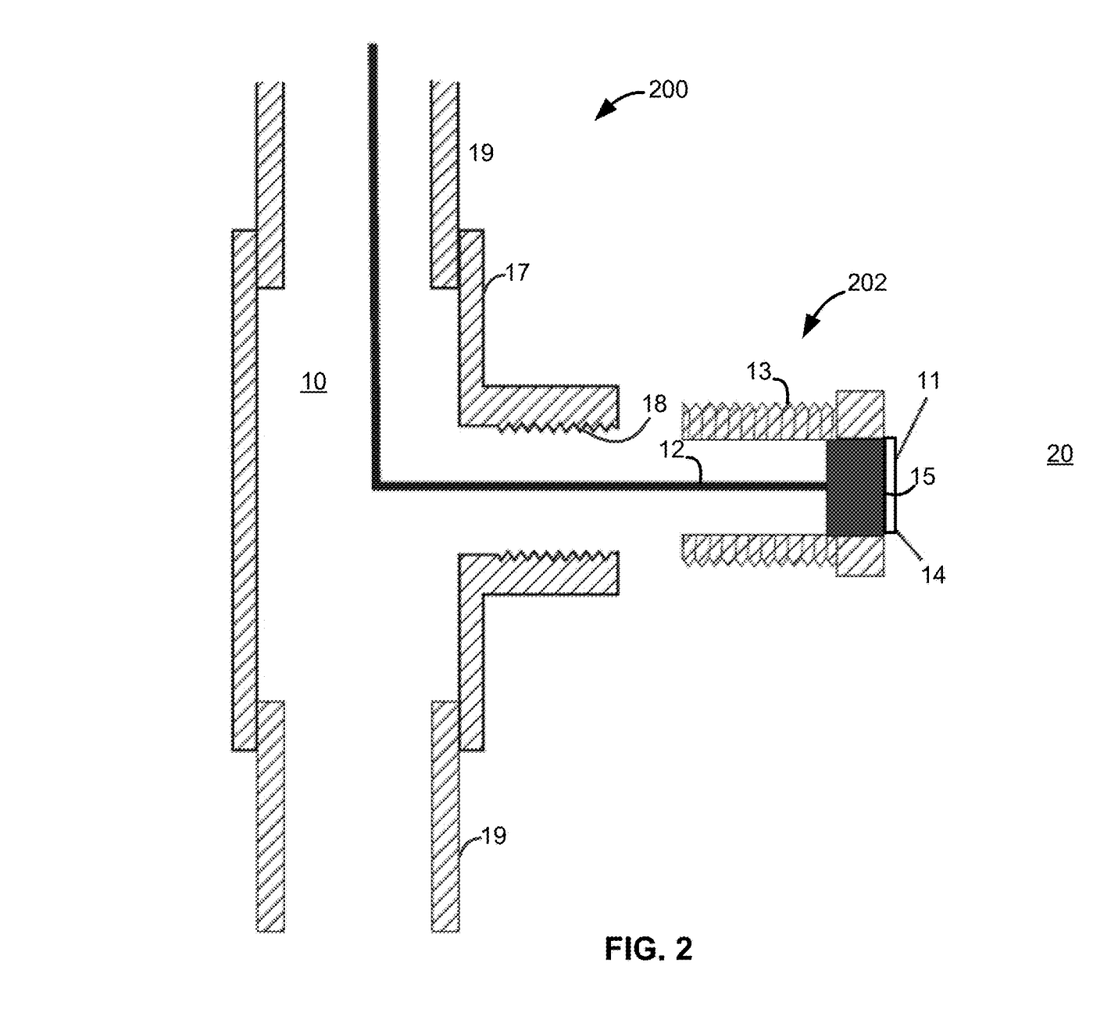
FIG. 2 illustrates an exemplary anode assembly suitable for monitoring solutions in natural or industrial environments located exterior to piping and/or a conduit in accordance with at least one embodiment of the disclosure.

Referring to FIG. 2, a microbial monitoring system 200, for monitoring a surrounding environment, e.g., water, solutions, sediments, soils, industrial environments, or the like, is illustrated. System 200 includes pipe 19 and anode assembly 202, which includes an anode 15. Pipe 19 can be used as a conduit to protect an anode cable 12 from an exterior environment 20. Anode cable 12 is passed through an interior 10 of the pipe 19. An anode 15 is located within a threaded fitting 13. The anode 15 is oriented within the threaded fitting 13 to monitor environments 20 exterior of the pipe 19. Unthreaded fittings and other methods of attachment may be used as an alternative to the threated fitting 13. The anode 15 can be composed of, for example, graphite, or other inert material (e.g., gold, titanium, or the like). A microbial biofilm 14 can populate the surface 11 of the anode 15. The anode cable 12 electrically connects to the anode 15. The threaded polymer fitting 13 connects to a threated port 18 of a tee fitting 17. The tee fitting 17 connects to the pipe 19. Multiple anodes may be deployed within the pipe 19 using multiple tee fittings 17.

Operation

The environment 20 interacts with the biofilm 14 located on the surface of the anode 11 creating a voltage. The anode cable 12 is used to transmit the voltage to, for example, a measurement device, described in more detail below.

Embodiment 3

Figure 3A:
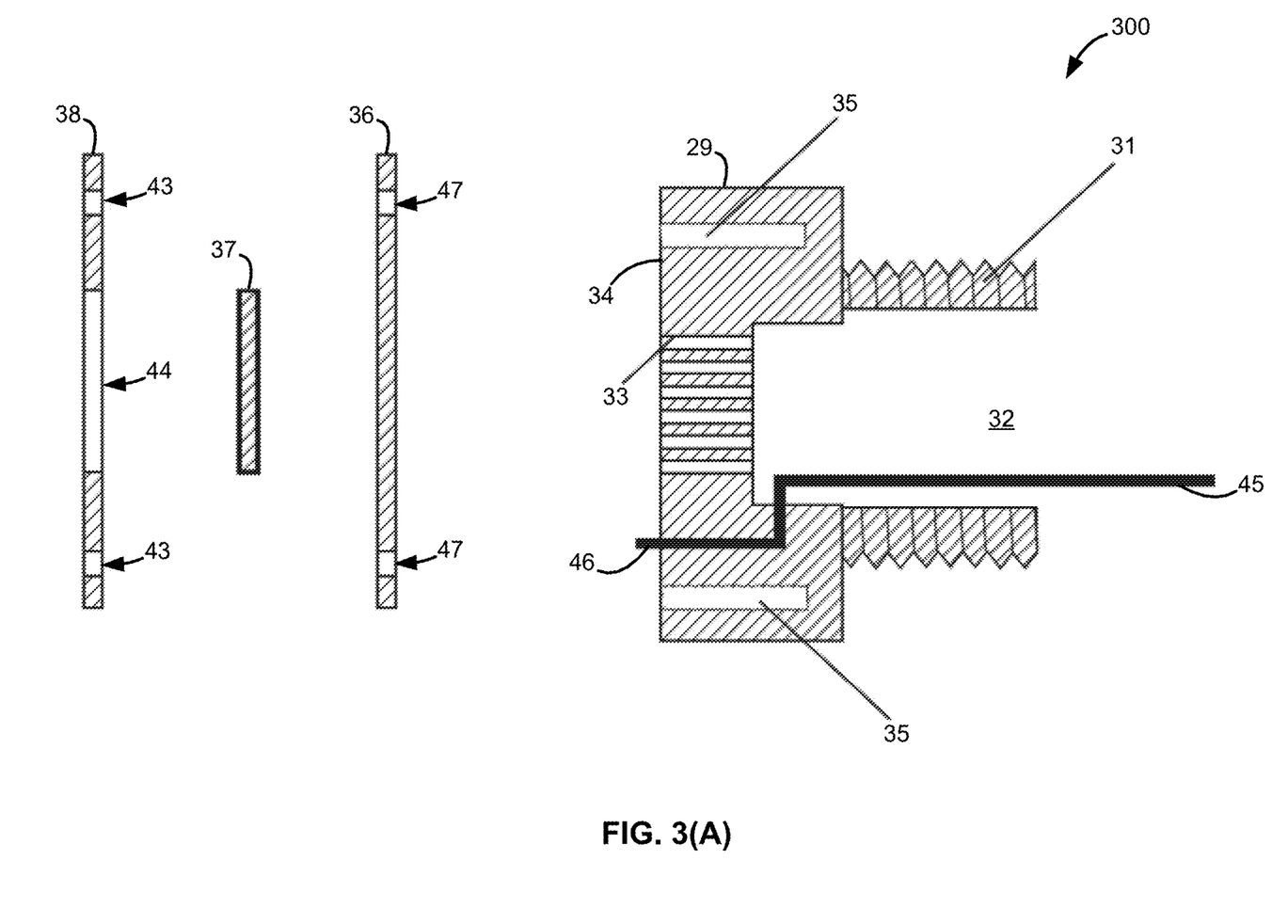
FIGS. 3(A) and 3(B) illustrate an exemplary reversible cathode assembly suitable for monitoring solutions and/or environments exterior of the piping and/or conduit in accordance with at least one embodiment of the disclosure.
Figure 3B:
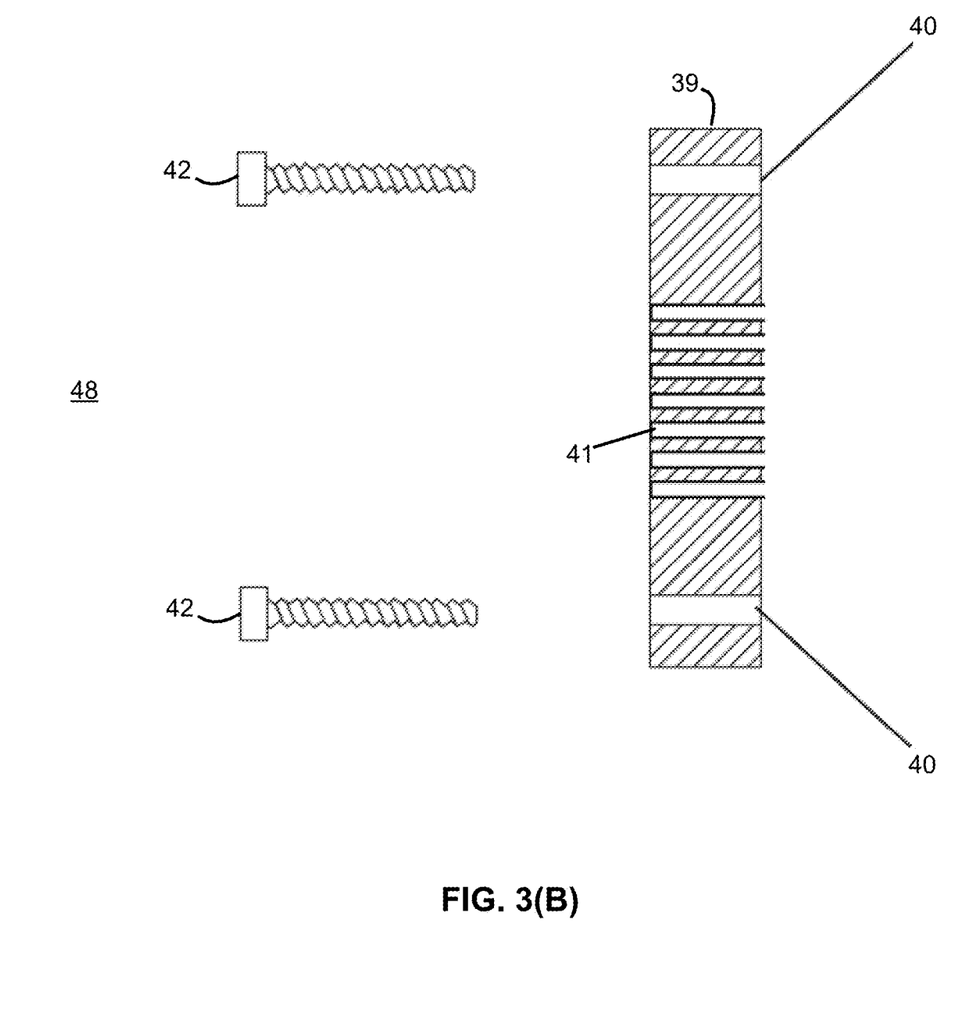

FIGS. 3(A) and 3(B) illustrate a reversible cathode assembly 300, including a body 29, a cathode 37, a gas-permeable membrane 36, and a cathode seal 38. The illustrated cathode assembly 300 uses a permeable membrane (e.g., available from several material supply houses including McMaster Carr) for the transport of oxygen from the atmosphere to the cathode. The design monitors solutions and/or environments exterior of the piping and/or conduit. Reversible cathode assembly 300 can be configured to monitor solutions and other media either 1) exterior of the piping/conduit (Embodiment 3) or 2) as reconfigured and within a pipe, as described below and illustrated in FIG. 4.

In the example illustrated in FIGS. 3(A) and 3(B), cathode assembly body 29 includes a threaded terminal end 31 and a (e.g., flat) surface 34 located opposite of the threaded terminal end 31. The surface 34 has a pattern of small holes 33 (e.g., having a diameter or similar cross section of about 0.05 to about 0.125 inches) passing through the surface 34 to an interior 32 of the body 29. The pattern of small holes 33 allows the diffusion of oxygen from the hollow interior 32 through the surface 34 of the cathode assembly body 29. An electrical contact 46 slightly extends beyond the surface 34 of the body 29. A cathode cable 45 electrically connects to the electrical contact 46 and to, for example, a measurement device, described in more detail below. The electrical contact 46 can be fabricated from an inert metal such a titanium, gold or platinum. The cathode cable 45 passes through the hollow interior 32 of the cathode assembly body 29 to, for example, a pipe connection.

Gas-permeable membrane 36, cathode seal 38, and cathode 37 can be secured against the surface 34 with a cathode frame 39, illustrated in FIG. 3(B). The cathode 37 fits within a cathode seal port 44 of the cathode seal 38. Cathode frame screws 42 are passed through cathode frame mounting holes 40, cathode seal mounting holes 43, and the gas-permeable membrane mounting holes 47. The cathode frame screws 42 can be used to fasten cathode frame 30 to cathode body mounting holes 35 to secure the cathode frame 39 with the cathode body 29. Securing the cathode frame 39 to the cathode body 29 can result in a waterproof seal, which can prevent an environment (e.g., water) 48 from entering the interior 32 of the cathode assembly body 29. Electrical contact 46 electrically contacts the cathode 37 after the cathode mounting screws 42 are secured to body 39.

A pattern of small holes 41 pass through the cathode frame 39. The environment 48 interacts with the cathode 37 through the pattern of small holes 41 of the cathode frame 39.

Operation

Oxygen passes from the interior 32 of the cathode assembly body 29 through the permeable membrane 36 to the cathode 37. The cathode 37 interacts with the environment 48 and the electrical contact 46 to provide the reference voltage. The reference voltage is transmitted from the electrical contact 46 through the cathode cable 45 to, for example a measurement device, such as a measurement device described herein.

Embodiment 4

Figure 4A:
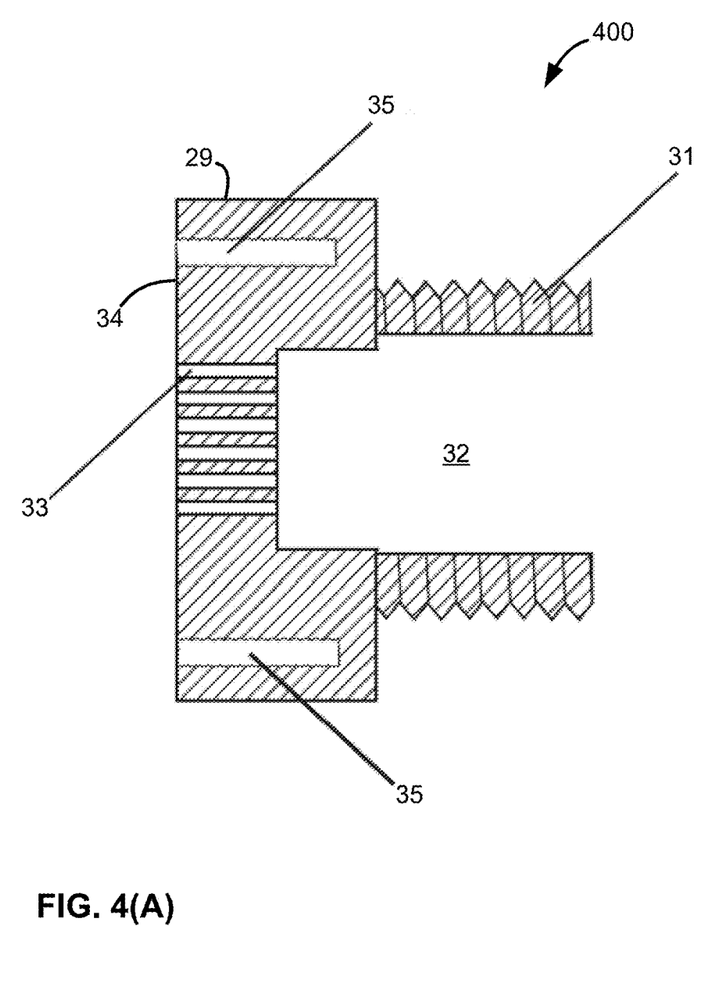
FIGS. 4(A) and 4(B) illustrate a reversible cathode assembly suitable for monitoring solutions located within the piping.
Figure 4B:
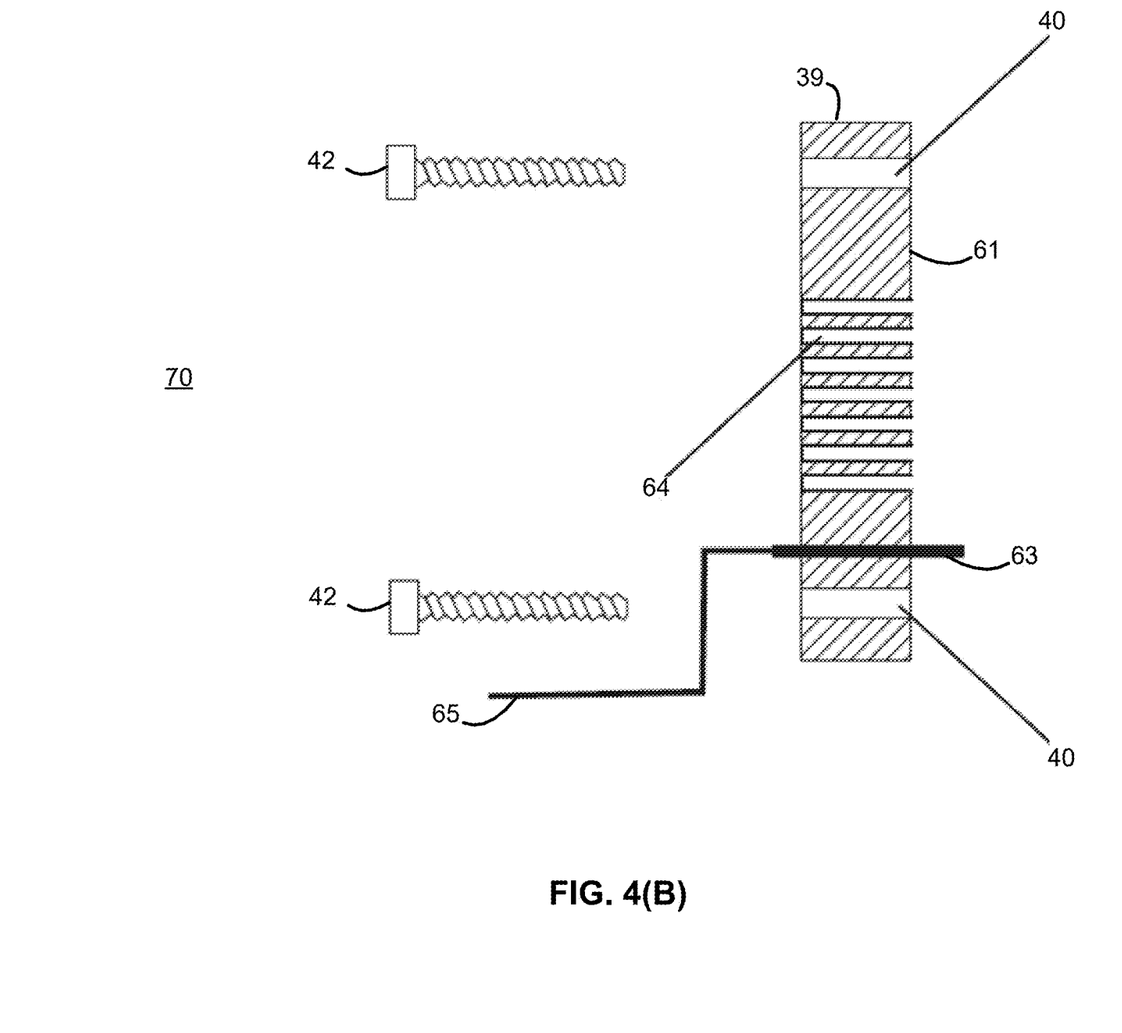

FIGS. 4(A) and 4(B) illustrate a configuration of reversible cathode assembly 400 for monitoring solutions located within the interior of the pipe. The cathode assembly 400 uses a permeable membrane for the transport of oxygen from the atmosphere to the cathode. This design monitors solutions located within the piping.

Reversible cathode assembly 400 is the same as cathode assembly 300, except the order of the gas-permeable membrane 36, a cathode seal 38, and a cathode 37 is changed, such that the cathode 37 is interposed between surface 34 and cathode seal 38, with the gas permeable membrane on an opposite surface of cathode seal 38 relative to the cathode 37. In this case, the pattern of small holes 33 allows solutions located within the hollow interior 32 of the body 29 to contact the cathode 37.

An electrical contact 63 slightly extends beyond a (e.g., flat) surface 61 of a cathode mounting frame 39. A cathode cable 65 electrically connects to the electrical contact 63. The electrical contact 63 is fabricated from, for example, an inert metal, such a titanium, gold or platinum.

The cathode mounting frame 39, illustrated in FIG. 4(B), has a pattern of small holes 64, allowing atmospheric oxygen 70 to pass through the cathode mounting frame 39 and contact a gas-permeable membrane 36.

As above, the gas permeable membrane 36, cathode seal 38, and cathode 37 are secured against the surface 34 of the body 29 with the cathode frame 39. The cathode 37 fits within a cathode seal port 44 of the cathode seal 38. Cathode frame screws 42 are passed through cathode frame mounting holes 40, cathode seal mounting holes 43 and gas-permeable membrane mounting holes 47. The cathode frame screws 42 fasten to body holes 35 to provide the pressure to secure the cathode frame 39 with the cathode body 29. The securing of the cathode frame screws 42 can form a waterproof seal preventing water within the interior 32 of the body 29 from passing to the atmosphere 70. The electrical contact 63 can electrically contact the cathode 37 after the cathode mounting screws 42 are secured.

Operation

Oxygen diffuses from the environment 70 through the small pattern of holes 64 of cathode frame 39 through the permeable membrane 36 to the cathode 37. The cathode 37 interacts with the solutions within the interior 32 of the body 29.

The electrical contact 63 provides the reference voltage. The reference voltage is transmitted from the electrical contact 63 and cathode cable 65 to, for example, a measurement device, as described herein.

Embodiment 5

Figure 5:
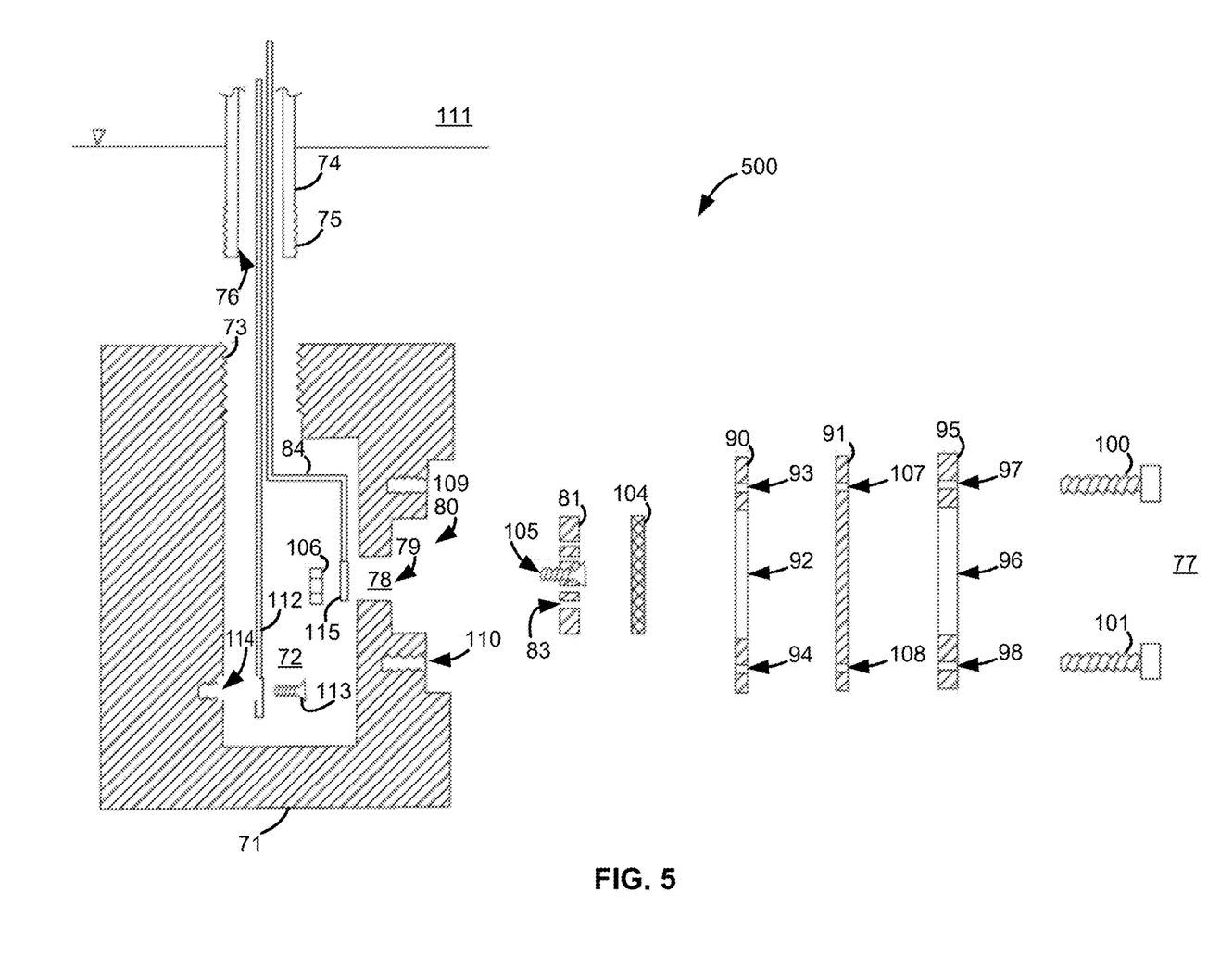
FIG. 5 illustrates a configuration of cathode assembly including an ion-specific membrane in accordance with at least one embodiment of the disclosure.

FIG. 5 illustrates a cathode assembly 500 in accordance with additional embodiments of the disclosure. Cathode assembly 500 includes a cathode body 71, a cathode mounting plate 81, a cathode 104, a cathode mounting seal 90, an ion-permeable membrane 91, and an exterior plate 95. The ion-permeable membrane 91 can be an ion-specific membrane that allows the transport of the hydrogen ion to the cathode.

The cathode body 71 is fabricated with a hollow interior 72. Threads 73 of the cathode body 71 connect to a threaded end 75 of a tube 74. Other forms of connection may be used to connect the tube 74 to the cathode body 71. A hollow interior 76 of the tube 74 connects with the hollow interior 72 of the cathode body 71 to form a pathway, allowing a free exchange of atmospheric oxygen 111 with a cathode 104. The combination of the hollow interior 76 of the tube 74 and the hollow interior of the cathode body 72 forms a snorkel.

The cathode mounting plate 81 connects to a cathode mounting port 79 located on a face of the cathode body 71 through a port 78 in the cathode body 71. A screw 105 attaches a cathode cable 84 to the cathode mounting plate 81 with a nut 106. The screw 105 electrically contacts the cathode 104. A pattern of small holes 83 pass through the cathode mounting plate 81. The cathode mounting plate 81 supports the cathode 104. The pattern of small holes 83 in the cathode mounting plate 81 provides a pathway for atmospheric oxygen 111 to pass from the hollow interior 72 of the cathode body 71 to the cathode 104.

The cathode 104 is positioned within a recess 92 within a cathode mounting seal 90 between the cathode mounting plate 81, an ion-permeable membrane 91 and an exterior plate 95. The cathode mounting seal 90, ion-permeable membrane 91, and the exterior plate 95 connect within the sealing port 80 of the cathode body 71 using mounting screws 100, 101. The mounting screws 100, 101 are passed through the mounting holes 93, 94 of the cathode mounting seal 90, the mounting holes 107, 108 of the ion-permeable membrane 91, and the mounting holes 97, 98 of the exterior plate 95. The screws 100, 101 are secured to mounting holes 109, 110 located in the sealing port 110 on the cathode body 101. Securing the mounting screws 100, 101 with exterior plate 95, cathode mounting seal 90, and ion-permeable membrane 91 to the cathode body 71 forms a water-proof seal preventing water from the environment 77 from entering the interior 72 of the of the cathode body 71.

The ion-permeable membrane 91 allows the transfer of hydrogen ions from the surrounding environment 77 through a port 96 located in the exterior plate 95. The cathode mounting seal 90 provides for a waterproof seal between the polymer membrane 91 and the cathode mounting port 80. The water-proof seal prevents water from the environment 77 entering in the interior 72 of the cathode body 71.

A leak detection cable 112 connects to the interior of the cathode body 71 with a screw 113 and a threated hole 114. The purpose of the leak detection cable 112 allows the detection of water within the interior 72 of the cathode body 71.

The ion-permeable membrane 91 can be fabricated with Nafion™ or other membranes allowing the transport of hydrogen ion through the membrane.

Operation

Oxygen passes from the atmosphere 111 through the interior 76 of the tube 74 and into the hollow interior 72 of the cathode body 71. The oxygen passes from the interior 72 of the cathode body 71 through the holes 83 of the cathode mounting plate 81 and interacts with the cathode 104.

Hydrogen ions from the environment 77 pass through the port 96 of the exterior plate 95 and pass through the ion-permeable membrane 91. The ions then pass to the cathode 104 and interact with the oxygen from the atmosphere 111.

The cathode 104 electrically connects to the screw 105. The electrical signal is transferred from the screw 105 to a connector 115 to the cathode cable 84. The cathode cable 84 transfers the electrical signal through the cathode body 71 and the tube 74.

Embodiment 6

Figure 6:
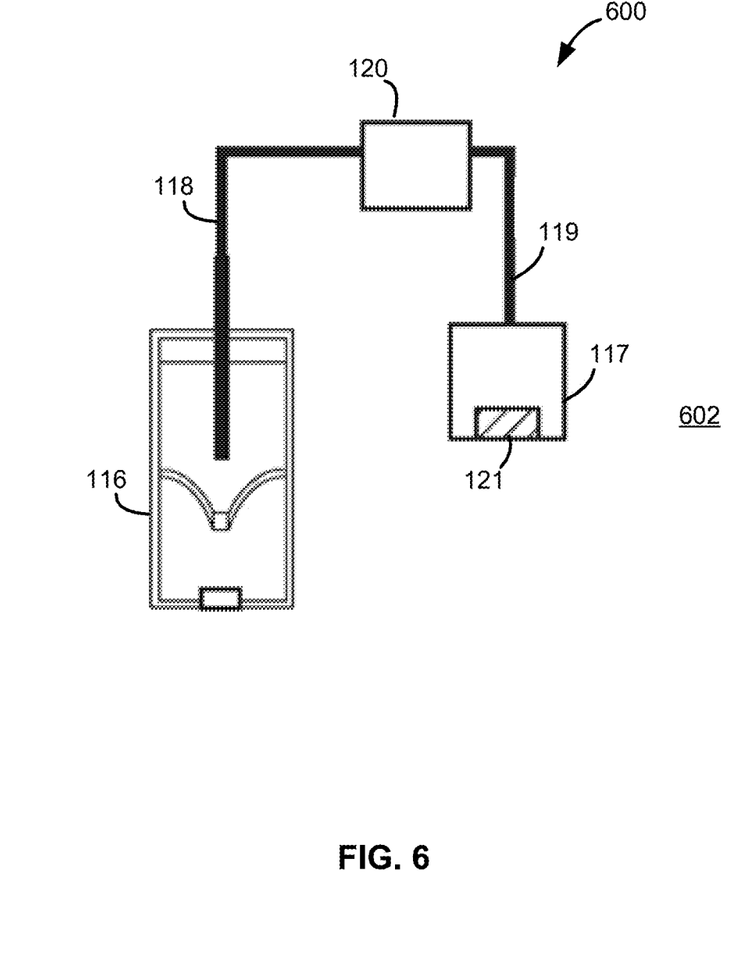
FIG. 6 illustrates a sensor system including a of a reference cell in accordance with at least one embodiment of the disclosure.

FIG. 6 illustrates a sensor system 600, sometimes referred to herein as s system, in accordance with exemplary embodiments of the disclosure. Sensor system 600 includes a first electrode (e.g., an anode) 117 in a first environment 602 to be monitored, a reference cell 116 (e.g., a standard reference cell), and a measurement device 120 electrically coupled to the first electrode and the reference electrode, wherein the measurement device measures a voltage between the first electrode 117 and the reference cell 116 to characterize microbial activity in the first environment 602. In accordance with various aspects of these embodiments, the voltage comprises an open-circuit voltage.

The illustrated embodiment uses a standard reference cell (such as silver/silver chloride or calomel) in lieu of a cathode when performing measurements of the environment 602. The reference cell 116 can be in a second environment (i.e., not in environment 602). Standard reference cells are commercially available.

A reference cell 116 electrically connects to an electronic circuitry/measurement device 120 with an insulated reference cable 118. First electrode (e.g., anode) 117 connects to the electronic circuitry 120 with an insulated anode cable 119. The surface of the anode 117 is populated with a biofilm 121. Multiple anodes may be connected to the electronic circuitry/measurement device 120.

Measurement device/electronic circuitry 120 can include, for example, high-impedance voltage measurements, 4-20 mA inputs and cellular communications.

Operation

This embodiment replaces the cathode with commercially-available reference cells. The measurement (e.g., open-circuit voltage) of the anode(s) 117 is measured against the reference cell 116 using measurement device 120 to determine microbial activity.

Embodiment 7

Figure 7:
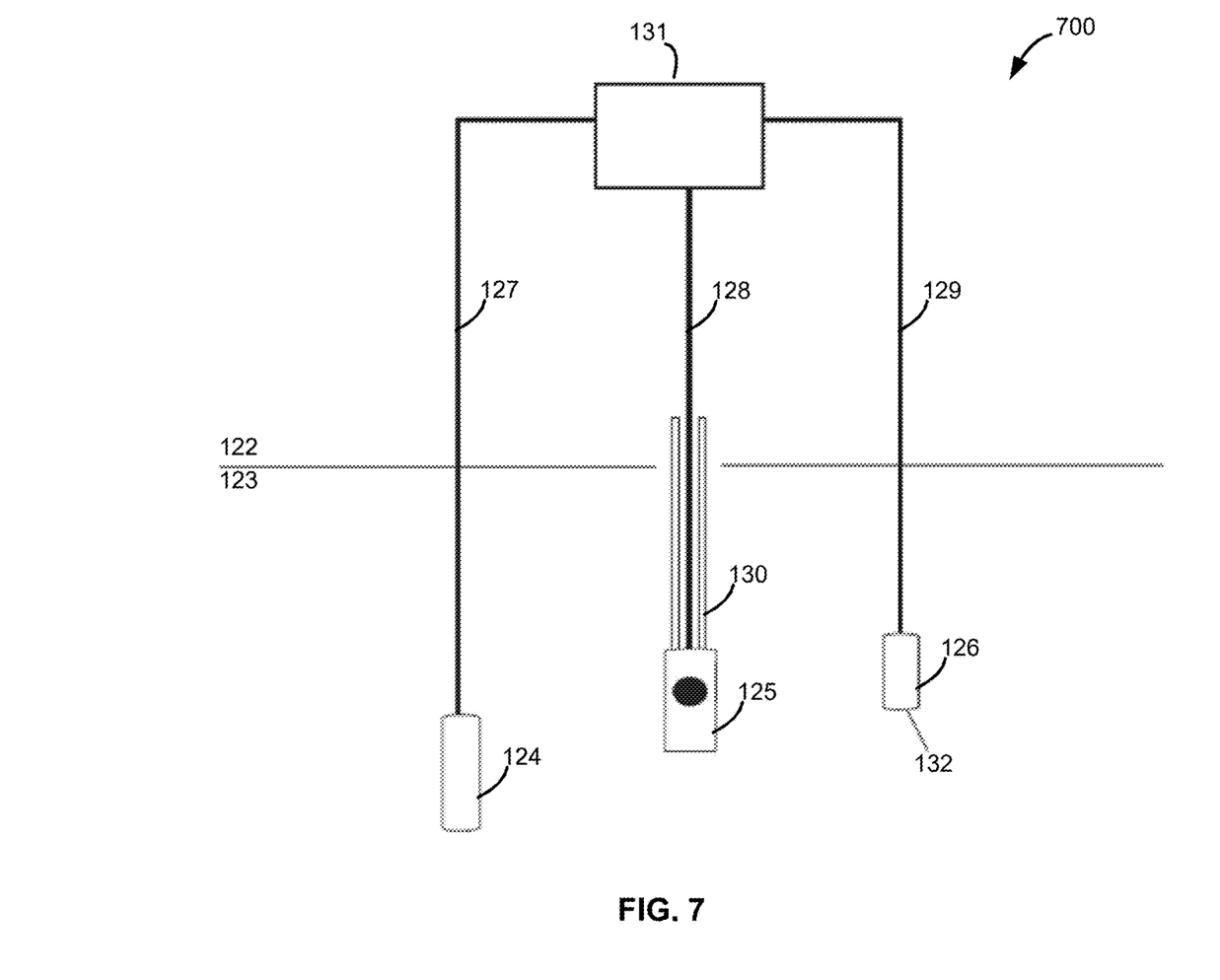
FIG. 7 illustrates a configuration of a microbial sensor system using a reference cell, a cathode, and one or more anode(s) in accordance with at least one embodiment of the disclosure.

Referring to FIG. 7, a sensor system 700 including a standard reference cell 124, a second electrode or cathode 125 and a first electrode or anode 126, is illustrated. The surface of the anode 126 is populated with a biofilm 132. In this case, standard reference cell 124 connects to the electronic circuit/measurement device 131 with an insulated reference cable 127. The standard reference cell may include, for example, an Ag/AgCl or a calomel reference cell. The cathode assembly 125 connects to the electronic circuitry/measurement device 131 with a cathode cable 128 through a tube 130. The anode cable 129 connects the anode 126 to the electronic circuitry/measurement device 131.

Operation

This embodiment allows the electronic circuitry/measurement device 131 to control the flow of current (e.g., automatically shunting through a 20000 to 500 ohm resistor) between the anode assembly 126 and cathode assembly 125, while the recovery voltage (OCV) is measured between the anode assembly 126 and the reference cell 124 to determine microbial activity on or proximate the anode 126.

Embodiment 8

Figure 8:
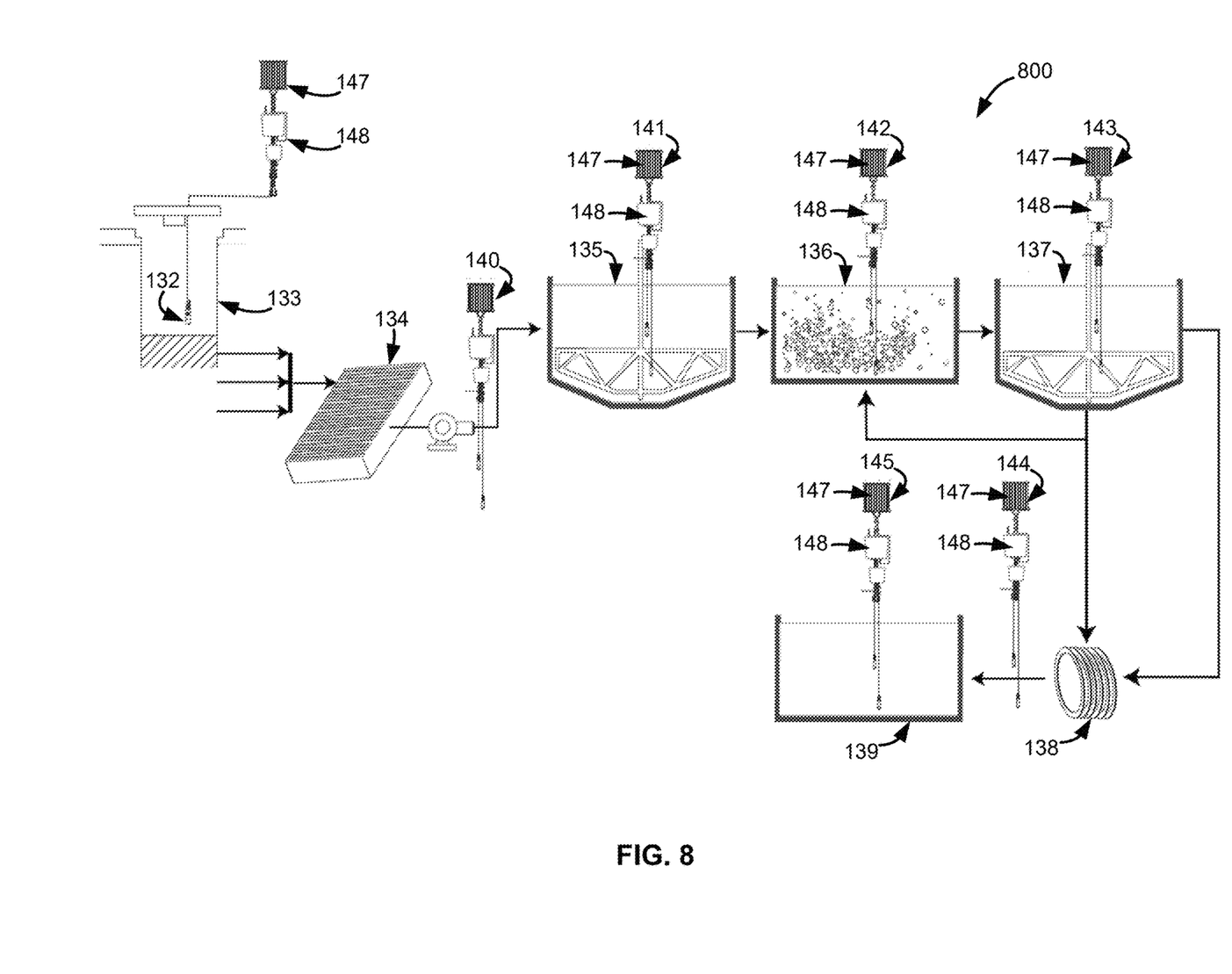
FIG. 8 illustrates a sensor system suitable for monitoring municipal and industrial wastewater treatment facilities using individual communication/control components transmitting the water quality data from microbial activity of each stage of a treatment facility to the internet in accordance with at least one embodiment of the disclosure.

Referring to FIG. 8, the embodiment illustrates a microbial sensor system 800 deployed at various locations—e.g., throughout a wastewater treatment facility. Examples of the disclosure can include any combinations of the illustrated sensors coupled to one or more measurement devices as described herein. In the illustrated example, a pretreatment microbial monitoring system 132 is located in a manhole 133. The pretreatment location may include lift stations and other locations where a microbial sensor may be deployed to monitor the wastewater before discharge into the treatment facility. A headworks microbial sensor system 140 is deployed at a headworks 134 of the facility. A settling basin microbial sensor system 141 is deployed at a primary settling basin 135. A reaction cell microbial sensor system 142 is deployed at a reaction cell 136. A secondary settling basin microbial sensor 143 is deployed at a secondary settling basin 137. A filter monitoring microbial sensor system 144 is deployed at a filtering operation of the facility 138. A disinfectant microbial sensor system 145 is deployed at the disinfectant operation of the facility 139.

The sensor systems can include a solar cell 147 and a signal/communication box 148. The solar cell 147 provides the power to the sensor system(s) and the signal/communication box 148 acquires the signal from one or more sensors—e.g., sensor 132. The signal is transmitted using cellular or other type of communications to transmit the data to a remote user. The data can be used to monitor and control the various processes to optimize (including the use of artificial intelligence) and improve the efficiency of the processes at the treatment facility.

We claim:

1. A sensor system comprising:
   a plurality of first electrodes in a first environment to be monitored;
   a biofilm formed overlying a surface of each of the first electrodes;
   a reference cell; and
   a measurement device electrically coupled to each of the first electrodes and the reference cell,
   wherein the measurement device measures an open circuit voltage between each of the first electrodes and the reference cell to characterize microbial activity in the first environment, wherein the first environment interacts with the biofilm on each of the first electrodes to create the open circuit voltage, and
   wherein the reference cell comprises a silver/silver chloride standard reference cell or a calomel standard reference cell.

2. The sensor system of claim 1, wherein the reference cell comprises an electrical contact, and wherein the electrical contact provides a reference voltage.

3. The sensor system of claim 1, wherein the reference cell is in the first environment.

4. The sensor system of claim 1, further comprising a lift station, wherein at least one of the first electrodes is disposed within the lift station.

5. The sensor system of claim 1, wherein the reference cell comprises the silver/silver chloride standard reference cell.

6. The sensor system of claim 1, wherein the reference cell comprises the calomel standard reference cell.

7. The sensor system of claim 1, wherein each first electrode of the plurality of first electrodes is in separate stations of a wastewater treatment facility and each first electrode of the plurality of first electrodes coupled to a signal/communication box to monitor and control the separate systems.

8. A method of measuring microbial activity, the method comprising the steps of:
   providing a plurality of first electrodes in a first environment to be monitored;
   populating each or the first electrodes with a biofilm;
   providing a reference cell; and
   measuring an open circuit voltage between each of the first electrodes and the reference cell to characterize microbial activity in the first environment,
   wherein the first environment interacts with the biofilm to create the open circuit voltage, and
   wherein the reference cell comprises a silver/silver chloride standard reference cell or a calomel standard reference cell.

9. A sensor system comprising:
   a first electrode in a first environment and having a biofilm formed thereon;
   a second electrode in a second environment having a biofilm formed thereon;
   a reference cell; and
   a measurement device electrically coupled to the first electrode, the second electrode, and the reference cell,
   wherein the measurement device measures an open circuit voltage between the first electrode and the reference cell to characterize microbial activity in the first environment and between the second electrode and the reference cell to characterize microbial activity in the second environment,
   wherein the first environment interacts with the biofilm formed on the first electrode to create the open circuit voltage between the first electrode and the reference cell and wherein the second environment interacts with the biofilm formed on the second electrode to create the open circuit voltage between the second electrode and the reference cell, and
   wherein the reference cell comprises a silver/silver chloride standard reference cell or a calomel standard reference cell.

10. The sensor system of claim 9, wherein the sensor system comprises a plurality of first electrodes in the first environment and coupled to the measurement device.

* * * * *